United States Patent
Levi et al.

(10) Patent No.: US 7,295,696 B2
(45) Date of Patent: Nov. 13, 2007

(54) AUTOMATIC OPTICAL INSPECTION SYSTEM AND METHOD

(75) Inventors: Michael Levi, Rehovot (IL); Bernard Solomon, Kfar Yona (IL); Doron Aspir, Modiim (IL); Elad Fridman, Tel Aviv (IL)

(73) Assignee: Orbotech Ltd., Yavne (IL)

( * ) Notice: Subject to any disclaimer, the term of this patent is extended or adjusted under 35 U.S.C. 154(b) by 0 days.

(21) Appl. No.: 11/711,100

(22) Filed: Feb. 27, 2007

(65) Prior Publication Data

US 2007/0154081 A1     Jul. 5, 2007

Related U.S. Application Data

(63) Continuation of application No. 10/327,115, filed on Dec. 24, 2002, now Pat. No. 7,203,355.

(51) Int. Cl.
*G06K 9/00* (2006.01)
*H04N 7/18* (2006.01)

(52) U.S. Cl. .................................. 382/145; 382/149

(58) Field of Classification Search .............. 382/147, 382/148, 149, 150, 151, 152, 145; 348/125, 348/126; 356/237.4, 237.5
See application file for complete search history.

(56) References Cited

U.S. PATENT DOCUMENTS 4,758,888 A    7/1988   Lapidot
4,803,735 A    2/1989   Nishida et al.
4,956,911 A    9/1990   Zaremba et al.
5,369,431 A    11/1994  Levy et al.
5,657,075 A    8/1997   Roessner
5,699,447 A    12/1997  Alumot et al.
5,784,484 A    7/1998   Umezawa
6,404,206 B1   6/2002   Sperschneider
6,434,264 B1   8/2002   Asar

FOREIGN PATENT DOCUMENTS

WO      WO 01/88592 A2    12/2001

OTHER PUBLICATIONS

Product Information on INSPIRE-9000™ Automated Optical Inspection System, Orbotech Ltd., Orbotech Website: http:www.Orbotech.com/products_mi_inspire9000.html, 2002.
Brochure: *INSPIRE-9000™Automated Optical Inspection System*, Orbotech Ltd., Israel, 1998.
Product Information on VRS-5™, Orbotech Ltd., Orbotech Website: http:www.Orbotech.com/products_mi_vrs.html, 2002.
Product Information on INFINEX-3000™, Orbotech Ltd., Orbotech Website: http:www.Orbotech.com/products_mi_infinex3000.html, 2002.
Brochure: *Vision-300AP™AOI Series*, Orbotech Ltd., Israel, 2000.
Brochure: *V-300 On-line Verification*, Orbotech Ltd., Israel, 1999.

*Primary Examiner*—Yon J. Couso
(74) *Attorney, Agent, or Firm*—Sughrue Mion, PLLC

(57) ABSTRACT

A system comprising automatic apparatus for automatic optical inspection (AOI), verification and correction of defects in an article, and a processor operative to select between AOI, verification and correction for performing on the article.

17 Claims, 5 Drawing Sheets

AUTOMATIC OPTICAL INSPECTION SYSTEM AND METHOD

FIELD OF THE INVENTION

This is a continuation of application Ser. No. 10/327,115 filed Dec. 24, 2002 now U.S. Pat. No. 7,203,355. The entire disclosure of the prior application, application Ser. No. 10/327,115 is hereby incorporated by reference.

The present invention relates generally to automatic optical inspection (AOI) systems, and particularly to a system and method for automatic optical inspection, verification and correction.

BACKGROUND OF THE INVENTION

Automatic optical inspection (AOI) systems are well known for the inspection of printed circuit boards (PCBs), flat panel displays (FPDs) and the like. AOI systems may be used to inspect various aspects and features of such articles during manufacture or assembly thereof, such as but not limited to, conductor integrity (breaks, continuity, cracking, etc.) and dimensions, insulator or substrate integrity and dimensions, hole size and placement, via size and placement, conductor pitch, line widths and lengths, artwork features, paste, component placement, solder joint defects and so forth.

After AOI, the article may typically be conveyed to a verification station for verifying whether defects discovered during inspection are real defects. If defects are verified as being real defects, the article may then pass on to a correction station for correcting those defects which are correctable (not all defects can be corrected). In the prior art, the verification station and the correction station comprise a unit which is located separately from the AOI unit.

SUMMARY OF THE INVENTION

The present invention seeks to provide a system and method for automatic optical inspection, verification and correction, which provides the possibility of performing inspection, verification and correction at one integrated station. This may significantly improve throughput of AOI systems, provide more flexibility in the manufacturing process and diminish or eliminate bottlenecks in the manufacturing flow.

There is thus provided in accordance with an embodiment of the invention an integrated system comprising automatic apparatus for automatic optical inspection (AOI), verification and correction of defects in an article, and a controller operative to transfer an article to be inspected between an AOI location and a verification and correction location. Preferably, AOI and verification and correction are performed simultaneously on two separate articles.

In accordance with an embodiment of the invention the automatic apparatus comprises a first station comprising an AOI device and a second station comprising a device operative to perform at least one of verification and correction of defects in the article.

Further in accordance with an embodiment of the invention the automatic apparatus comprises a first station comprising an AOI device, a second station comprising a verification device operative to verify defects in the article, and a third station comprising a correction device operative to correct defects in the article.

Still further in accordance with an embodiment of the invention a conveyor is provided for conveying an article between the first and second (and third) stations.

Still further in accordance with an embodiment of the invention, AOI comprises an image acquisition assembly including a plurality of illuminators and a plurality of sensors generally extending across the entire width of an article to be inspected, such that an article to be inspected may be inspected by a single non-interrupted pass past the image acquisition assembly in a first direction and then removed from the AOI by transporting the inspected article in a second direction generally opposite to the first direction.

There is also provided in accordance with an embodiment of the invention a system for the automatic optical inspection (AOI) of articles comprising an illumination and image acquisition subsystem, a first support surface operative during a first time interval to support a first article to be inspected and to transport the first article past the image acquisition subsystem in single uninterrupted pass to acquire an image thereof, and a second support surface operative during the first time interval to receive a second article to be inspected at a location away from the image acquisition subsystem.

Further in accordance with an embodiment of the invention, the second surface is operative during a second time interval to support the second article and to transport the second article past the image acquisition subsystem in single uninterrupted pass to acquire an image thereof, and the first support surface is operative during the second time interval to enable the first article to be removed therefrom and to receive a third article to be inspected at a location away from the image acquisition subsystem.

Still further in accordance with an embodiment of the invention, the illumination and image acquisition subsystem is arranged along an axis extending generally perpendicularly to an axis of transport of the first and second support surfaces.

There is also provided in accordance with an embodiment of the invention a method for manufacturing printed circuit boards comprising providing automatic apparatus for automatic optical inspection (AOI), verification and correction of defects in an article, performing AOI on a first printed circuit board substrate, and generally simultaneously to performing verification and correction of suspected defects, previously found by AOI, on a second printed circuit board substrate.

In accordance with an embodiment of the invention the method further comprises performing another manufacturing step after performing at least one of AOI, verification and correction on the article.

Further in accordance with an embodiment of the invention the method further comprises diverting the article to another workstation while continuing to perform at least one of AOI, verification and correction on the article.

BRIEF DESCRIPTION OF THE DRAWINGS

The present invention will be understood and appreciated more fully from the following detailed description taken in conjunction with the drawings in which.

DETAILED DESCRIPTION OF PREFERRED EMBODIMENTS

Figure 1:
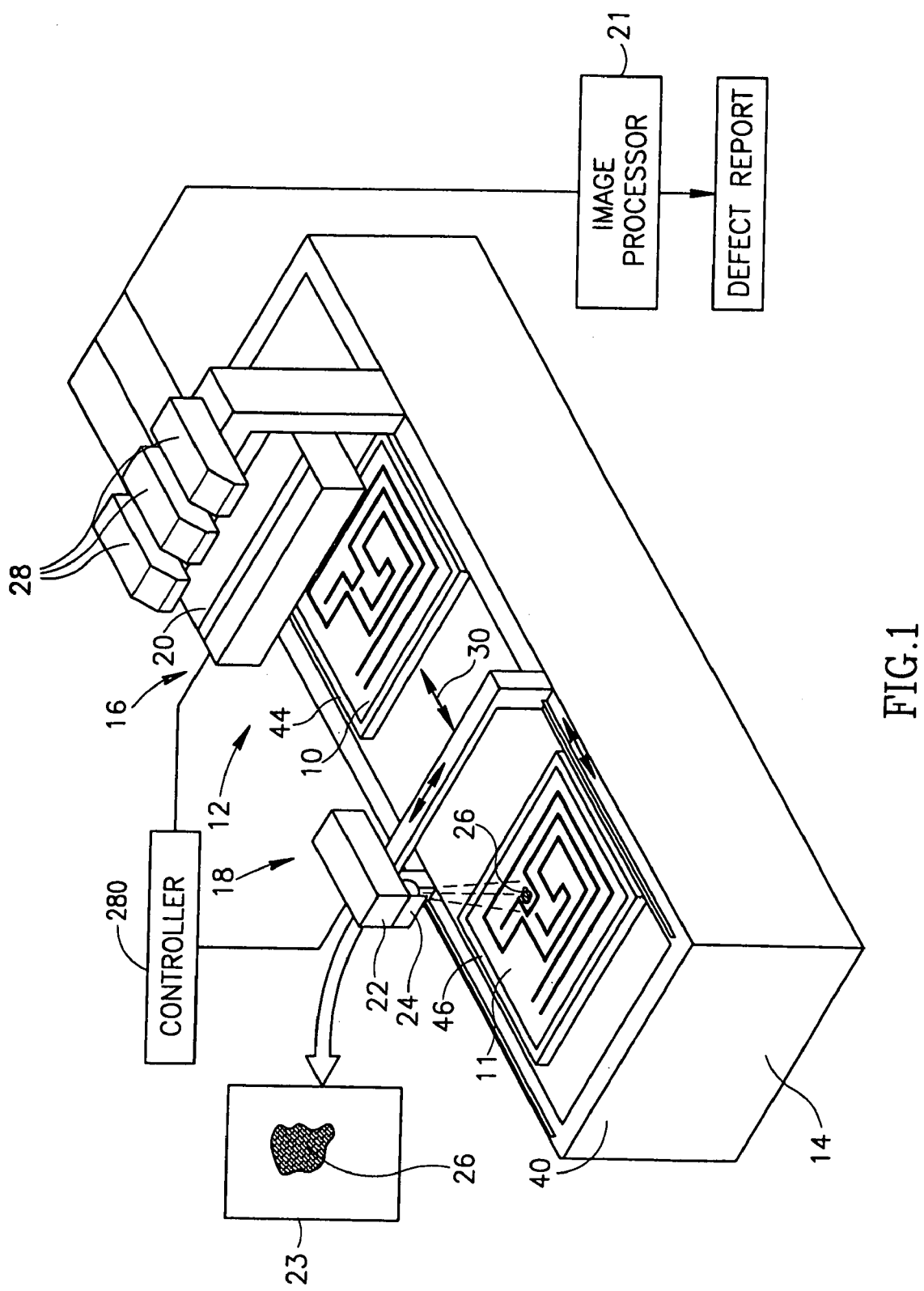
FIG. 1 is a simplified pictorial illustration of a system for automatic optical inspection, verification and correction of articles, constructed and operative in accordance with an embodiment of the present invention.

Reference is now made to FIG. 1, which illustrates an integrated system for automatic optical inspection, defect verification and correction of one or more articles 10, constructed and operative in accordance with an embodiment of the present invention. Articles 10 may comprise, without limitation, electrical circuits such as printed circuit boards (PCBs), flat panel displays (FPDs), chip interconnect packaging (ICPs) and the like.

The system may comprise, for example, automatic apparatus 12 having a chassis 14 defining an inspection location 16 whereat possible defects in article 10 may be identified, for example by means of automatic optical inspection (AOI), and a defect verification and correction location 18 whereat the possible defects in article 10 may be evaluated as being real or false defects, and corrected, as needed.

In the embodiment seen in FIG. 1, automatic apparatus 12 comprises an AOI device 20 at inspection location 16, and a verification device including an imaging functionality, designated 22, configured to enable the correction of at least some defects, for example by providing a sufficient working distance between an article 11 and the imaging functionality such that a defect can be corrected manually such as by scraping away extraneous copper, at defect verification and correction location 18.

AOI device 20 is operative to inspect a first article 10 to find possible defects therein, some of which may be real defects and some of which may be false defects. Verification device 22 is operative to provide at least one of the following functionalities with respect to an inspected article 11 that has been inspected by AOI device 20: acquiring and displaying an image 23 of a possible defect in inspected article 11 such that an operator may determine whether a possible defect is in fact a real defect or a false defect, and enabling the operator to correct a correctable real defect; automatically verifying whether a possible defect found in article 11 is a correctable real defect, a non-correctable real defect or a false defect, for example by analysis of relatively high resolution image acquired by verification device 22; correcting correctable real defects in article 11; and discarding articles 11 that have non-correctable real defects. Typical examples of correctable real defects include, for example and without limitation, conductors having various protrusions some of which may result short circuits, copper splashes and the like. Examples of non-correctable real defects may include, for example and without limitation, certain missing features, and conductors having a severe nick, a non-localized improper width, breaks along conductors and the like.

In accordance with an embodiment of the invention, a correction functionality associated with verification device 22 is performed manually by an operator, or optionally automatically.

In accordance with an embodiment of the invention, verification device 22 is operative such that the imaging functionality displays an image 23 of a defect which is used by an operator to quickly identify false defects before removal of an inspected article from automatic apparatus 12. Additionally, the imaging functionality may be used by an operator while correcting inspected article 11 before removal from automatic apparatus 12.

In accordance with an embodiment of the invention, a suitable computer image processor may provide an automatic false defect filtering functionality. Articles 11 having non-correctable real defects may be discarded. Articles 11 having correctable real defects may be corrected before removal from automated apparatus 12 or passed on to a separate correction station along with an indication of each of the correctable real defects in the article. The locations of false defects are discarded such that only correctable real defects need be considered at a correction station.

In accordance with an embodiment of the present invention, verification device 22 is configured such that correction may be performed at verification and correction location 18. Thus in accordance with an embodiment of the invention, verification device 22 is positioned at a sufficient distance from article 11 such that an operator may access article 11 to perform defect correction while simultaneously viewing an image 23 of a portion of article 11 being corrected. Optionally, an automated functionality, designated defect corrector 24, is provided to automatically correct at least some defects in article 11. A typical defect that may be corrected is excess copper such as at a copper splash 26 in a printed circuit board, shown in image 23.

AOI device 20 typically comprises illumination and image acquisition apparatus (not shown), such as but not limited to, back-lighting and/or top-lighting apparatus, for illuminating article 10 during inspection thereof. Article 10 may be inspected with incoherent or coherent light, for example. A preferred embodiment of illumination apparatus suitable for use in AOI device 20 is described in copending U.S. patent application Ser. No. 09/719,728 entitled "Illuminator for Inspecting Substantially Flat Surfaced", filed Dec. 13, 2000 as a national phase application of PCT/IL98/00285 filed Jun. 16, 1998, the disclosure of which is incorporated by reference in its entirety.

AOI device 20 may further comprise image acquisition apparatus 28, such as but not limited to, at least one CCD (charge coupled device) array. In the embodiment seen in FIG. 1, three side-by-side image acquisition apparatuses 28, each associated with a CCD or CMOS based imager, are provided such that as an article 10 is transported past the image apparatuses 28, for example in the direction of arrow 30, several image swaths (in the example shown three, each associated with a corresponding image acquisition apparatus 28) of article 10 are acquired simultaneously. In this manner, an image of substantially the full width of article 10 may be acquired from a single uninterrupted pass of article 10 by AOI device 20.

Different features on article 10 may reflect the illuminated light at different intensities. For example, conductors (typically copper lines) may reflect the light at a higher intensity than the duller substrate. Thus, the features (e.g., conductors and substrate) may be recognized by an intensity of their reflected light.

In accordance with an embodiment of the invention, a computer image processor 21, in operational communication with AOI device may output a report indicating suspected defects in article 10. The computer image processor 21 may include, for example, hardware image processing components as well as software image processing programs running on one or more computer workstations.

Examples of an AOI device 20 that may be adapted for use in a system operating according to an embodiment of the present invention include, without limitation, InSpire-9000™, SK-75™, and InFinex™ series of automatic optical inspection systems, commercially available from Orbotech Ltd., Yavne, Israel. These systems may be used to inspect PCB substrates having features and components, such as without limitation, complex fine lines or ball grid arrays (BGAs).

The acquisition of images of possible defects in article 11, such as those found by AOI device 20, may be carried out at defect verification and correction location 18 by various devices, such as but not limited to, an autofocus video camera, configured for example as an autofocus video microscope 39 as generally described in copending U.S. patent application Ser. No. 09/570,972 entitled "Microscope Inspection System", filed Jun. 15, 2000, the disclosure of which is incorporated by reference in its entirety. Video microscope 39 may be spaced from an item on article 11, e.g., an electrical circuit, located at defect verification and correction location 18 by a distance which enables physical access to the electrical circuit for correction thereof.

In accordance with an embodiment of the present invention, the defect verification and/or correction functionality of defect verifier 22 is generally operative on an article 11 simultaneously to the inspection of defects in article 10 by AOI device 20 at inspection location 16. Thus, in the embodiment seen in FIG. 1, a first conveyor (not shown) is provided for conveying an article, such as article 10, on a first support surface (or table, the terms being used interchangeably) 44 between the various stations. A second conveyor (not shown) may also be provided for conveying an article, such as article 11, on a second support surface (or table, the terms being used interchangeably) 46 between the various stations. The first and second support conveyors in combination with the first and second support surfaces may also be considered as positioners operative to selectably position articles at one of the stations 16 and 18. In accordance with an embodiment of the invention, in order to accommodate simultaneous inspecting of article 10 at inspection location 16 and verification of article 11 at verification and correction station 18, the respective conveying paths of article 10 and article 11 are non-identical.

Thus, in accordance with an embodiment of the present invention, a first support table 44 supporting article 10 is transported in a first conveying plane. A second support table 46 supporting article 11 is transported in the first conveying plane at inspection station 20, however to and from inspection station 20 the second support table 46 is at least partially in a second conveying plane generally parallel to first conveying plane.

Reference is now made to FIGS. 2A-2I which are schematic side view diagrams illustrating the operation of an integrated system for inspection, verification and correction of articles in accordance with an embodiment of the present invention. Each of FIGS. 2A-2I schematically show a chassis 114, an inspection location 116, a defect verification and correction location 118, an AOI device 120, a verification device 122, a first support table 144, and a second support table 146. The first support table 144 and second support table 146 support, respectively, articles to be inspected during inspection and subsequent verification and correction.

Figure 2A:
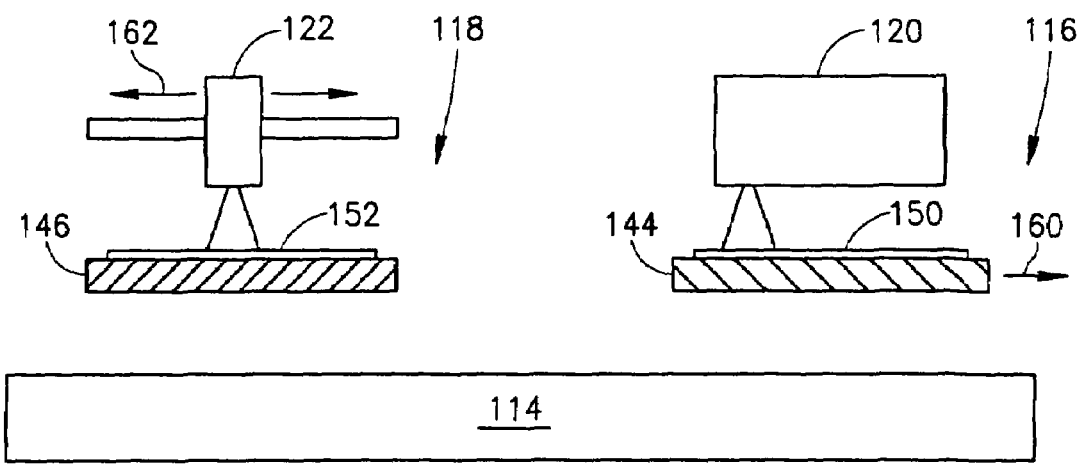
FIGS. 2A-2I are simplified block diagrams illustrating operation of the system of FIG. 1.

In FIG. 2A, a first article to be inspected, designated 150, is supported by support table 144 and is shown being transported in the direction of arrow 160 during automated optical inspection by AOI device 120. Generally during the time interval required by AOI device to automatically optically inspect first article 150 for defects, a second article 152 is supported by second support table 146 at verification location 118 while verification device 122 is operative to move, as indicated by arrows 162, to locations of suspected defects. Verification device 122 is operative to acquire an image of suspected defects (not shown), which typically are displayed to an operator. It is noted that the performance of a verification functionality at verification location 118 is optional. In some embodiments of the invention, verification location 118 is used solely for loading and offloading articles from one of the support tables 144 and 146 during the time interval used to inspect an article loaded on the other support table, without performing a verification or correction functionality thereat.

Figure 2B:
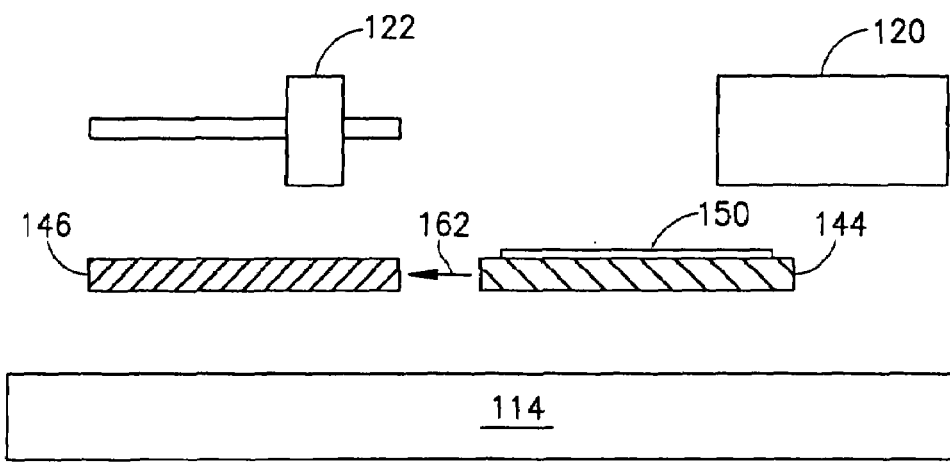

As seen in FIG. 2B, upon the completion of automated optical inspection by AOI device, or upon verification and/or correction of all suspected defects in second article 152 by verifier 122, the second article 152, which has been both inspected and defects therein at least partially verified, has been removed from the second support table (and is not shown in FIG. 2B) and a third article 154 (seen in FIG. 2C) is placed on second support table 146. The first support table 144, which bears a now automatically optically inspected first article 150 is transported toward verification and correction location 118 in the direction of arrow 162.

Figure 2C:
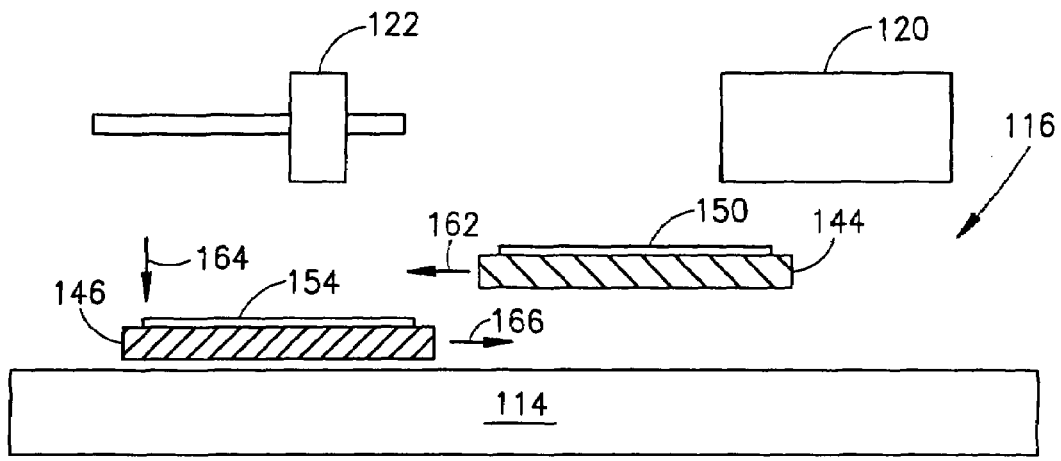

Next, as seen in FIG. 2C, the first support table 144, which remains disposed at a first level, continues to be transported in the direction of arrow 162. The second support table 146, now bearing third article 154, drops down, as indicated by arrow 164, to a second level disposed below the level of first support table 144, and is transported toward inspection location 116 in the direction indicated by arrow 166.

Figure 2D:
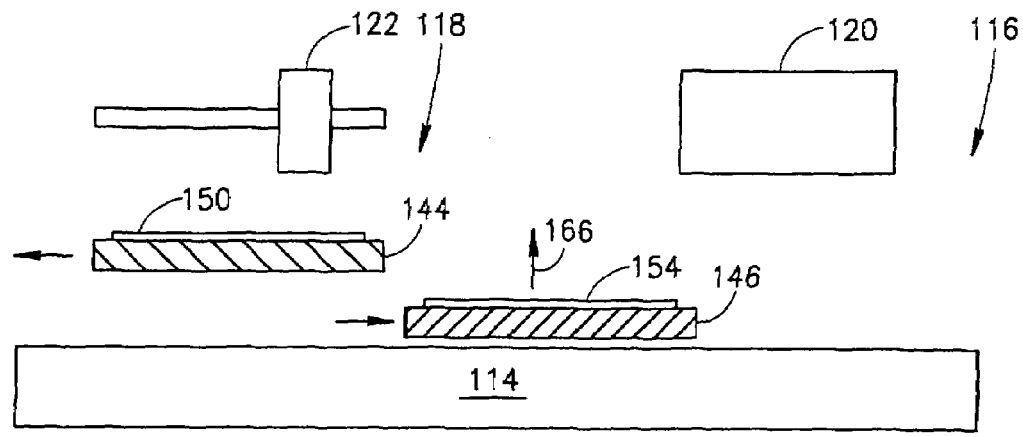

As seen in FIG. 2D, once second support table 146 clears the first support table 144, but generally before reaching inspection location 116, it is lifted up as indicated by arrow 166 to a level required by AOI device 120 to conduct automated optical inspection.

Figure 2E:
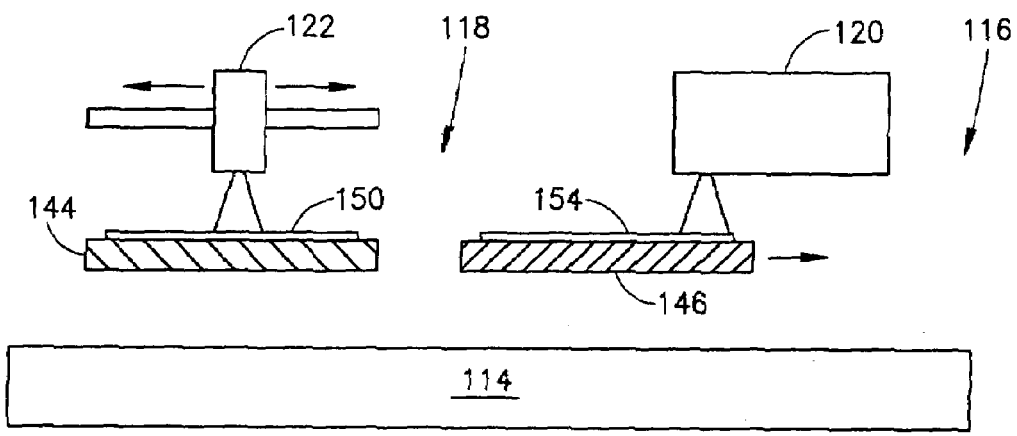
Figure 2F:
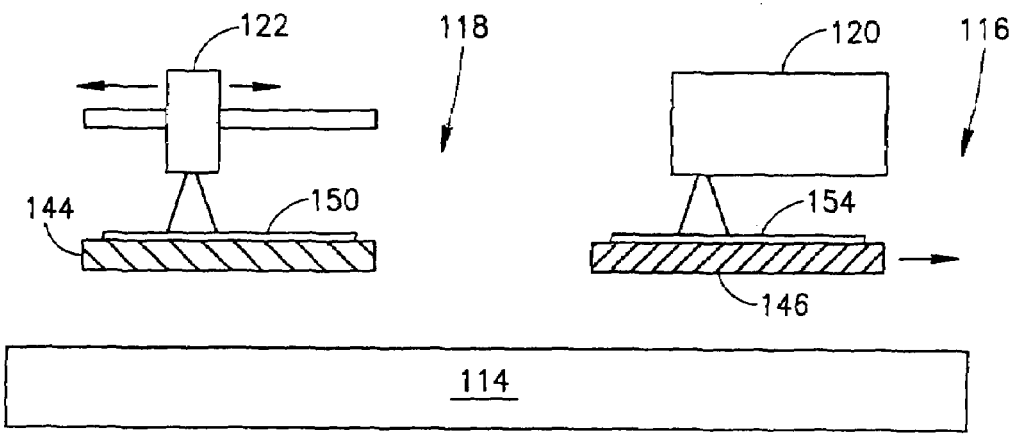

As seen in FIGS. 2E and 2F respectively, once first support table 144 reaches verification and correction location 118 and once second support table 146 reaches AOI location 116, the third article 154 is automatically inspected for suspected defects with AOI device 120 while generally simultaneously suspected defects on first article 150 are verified and corrected.

Figure 2G:
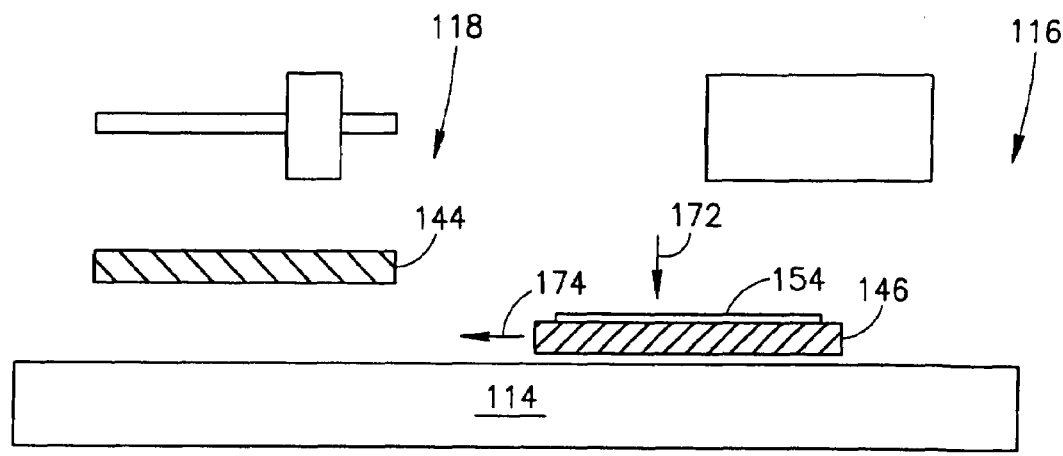
Figure 2H:
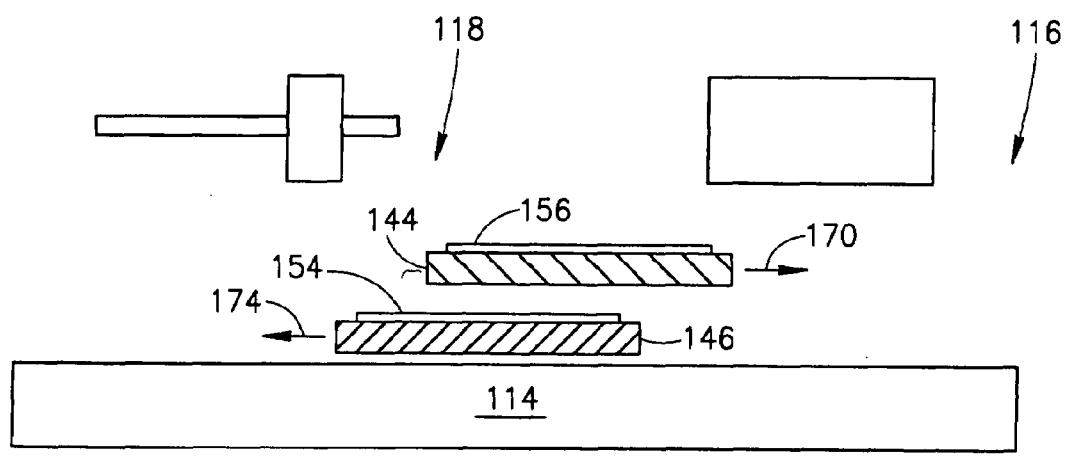

As seen in FIGS. 2G and 2H, once the verification and correction of selected suspected defects on first article 150 is completed, the first article 150 is removed from first support table 144 and replaced by a fourth article 156 (FIG. 2H). The first support table 144 is then transported in the direction of arrow 170 to inspection location 116. Once the automated optical inspection of third article 154 is completed, second support table 146 is dropped down to a level below first support table 144, as indicated by arrow 172, to clear first support table 144, and is transported away from inspection location 116 in the direction indicated by arrow 174.

Figure 2I:
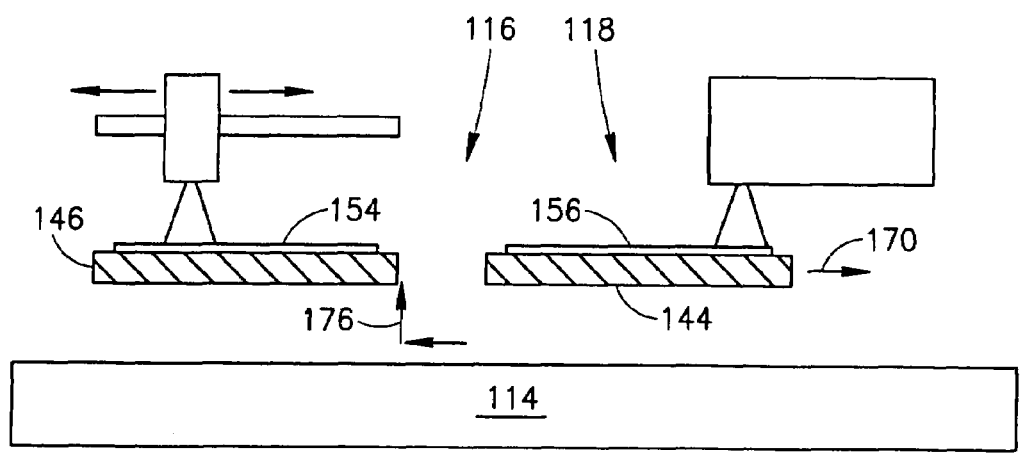

Completion of the cycle is seen in FIG. 2I, wherein second support table 146 is raised to a level suitable for verification and correction of suspected defects at verification location 118, as indicated by arrow 176. Generally simultaneously to the verification and correction of suspected defects on third article 154, first support table 144 is transported past AOI device 120 at inspection location 118, in the direction of arrow 170, to inspect fourth article 156 for suspected defects.

It is noted that in accordance with an embodiment of the invention, the relative time intervals for inspection and for verification and correction are mutually interdependent and may be adjusted, for example to accommodate inspection process constraints. Thus in accordance with an embodiment of the invention, the verification and correction may be made time dependent on the time interval required to inspect an article for defects at inspection location 116. In such a configuration, only those suspected defects that can be verified and corrected during a time interval required to perform AOI are handled. If non verified suspected defects remain following the completion of AOI, then an article one which some suspected defects have been verified and other have not been verified is passed on to an offline verification and correction station where any remaining suspected defects are then verified. It is appreciated that in this mode of operation, the load at a stand alone verification and correction station is substantially reduced, although it may not be entirely eliminated.

Alternatively, the integrated system may be configured to be dependent on the time interval required to verify and correct all suspected defects on an article. In such a mode of operation, should the time interval required to verify and correct defects and to place a new article on a support table exceed the time interval required to inspect an article for defects at inspection location 116, then the return transport of an inspected article from inspection location 116 to verification location 120 may be delayed. Thus, this mode of operation may be slower than a mode of operation by which operation of the integrated system is constrained by AOI, however each article handled by the system is inspected, verified and corrected thereby eliminating the need for a stand-alone verification and correction station.

Figure 3:
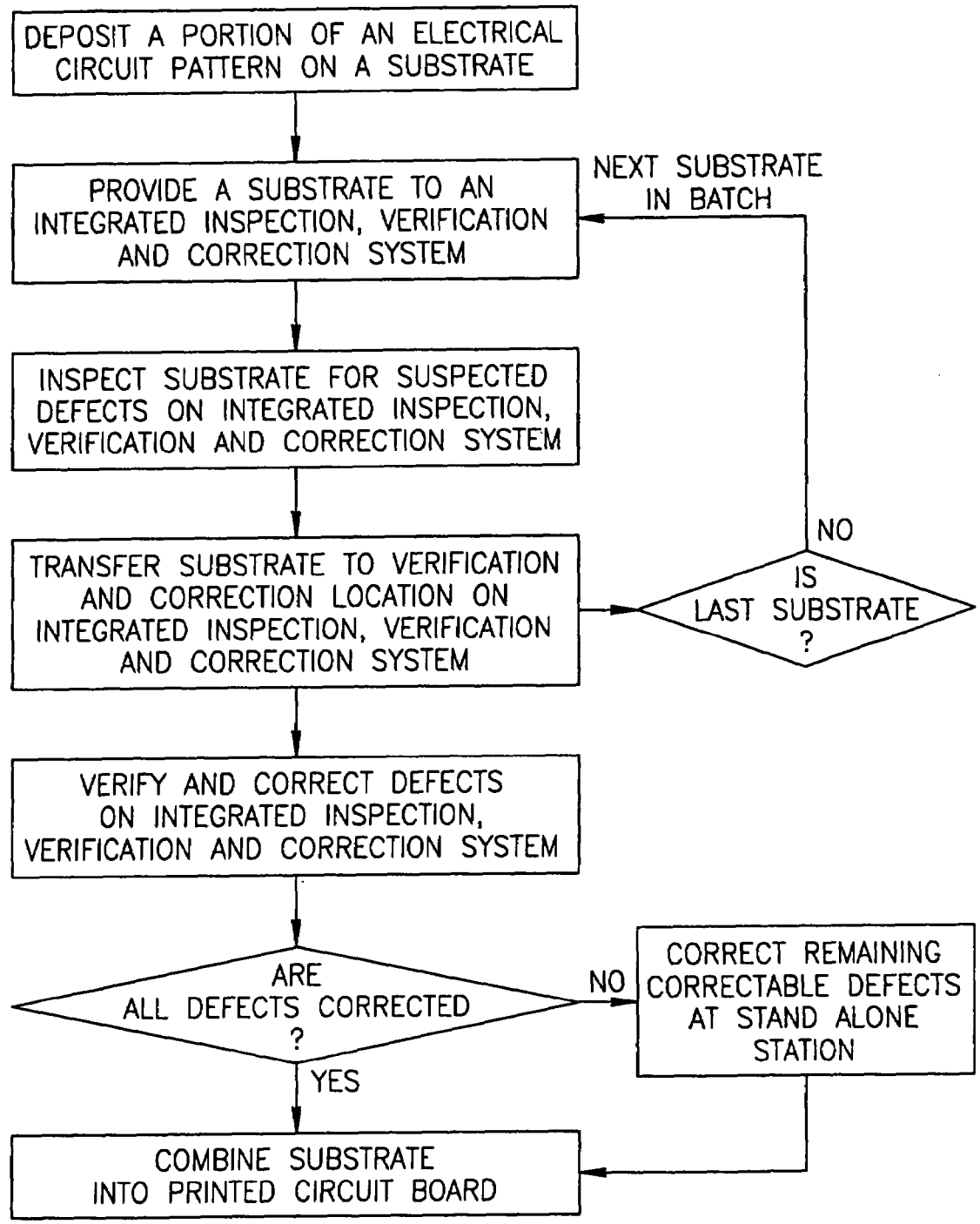
FIG. 3 is a simplified flowchart of a method for manufacturing printed circuit boards in accordance with an embodiment of the present invention.

Reference is now made additionally to FIG. 3, which illustrates a method for manufacturing printed circuit boards using an integrated system for automatic optical inspection, verification and correction of articles, in accordance with an embodiment of the present invention.

A controller 280 (FIG. 1) may be in communication with first and second locations 16 and 18 and tables 44 and 46, and may control the flow of operation of the system. Processor 280 may select between which of the operations— AOI, verification and correction—are to provide a constraint for completion of inspection, verification and correction of an article 10, namely whether articles offloaded from the system are to be partially or fully verified and corrected.

In accordance with an embodiment of the present invention, a portion of an electrical circuit pattern is deposited on a substrate, such as a printed circuit board substrate. Typically substrates are prepared in a batch, and each of the substrates in the batch is provided with the same portion of an electrical circuit pattern.

Each substrate in a batch of substrates is provided serially to an integrated inspection, verification and correction system such as system 12 (FIG. 1), whereat a substrate is transported to an inspection location and automatically optically inspected to ascertain the presence and respective locations of anomalies suspected of being defects. In accordance with an embodiment of the invention, during at least part of the time that a first substrate is being automatically optically inspected, a new substrate is loaded onto the integrated system.

After completion of automatic optical inspection of a substrate, an automatically optically inspected substrate is transferred to a defect verification and correction location located on the integrated system where its suspected defects are verified as being real defects or are determined to be false defects, and correctable real defects are corrected. In accordance with an embodiment of the invention, verification and correction of suspected defects on an inspected substrate is performed generally simultaneously with the inspection of a new substrate.

If at least some of the suspected defects have not been either verified or corrected, the substrate is passed on to a stand alone verification and correction station, for example a VRS-4 verification station available from Orbotech Ltd. of Yavne, Israel, where suspected defects on the substrate are finally verified and, as needed, corrected. Substrates having uncorrectable defects are discarded. It is appreciated that a significantly reduced quantity of defects reach the stand alone verification and correction station, as compared with conventional inspection, verification and correction methods.

Once suspected defects are all verified and corrected the substrate is removed from the integrated system. If all of the suspected defects have been verified and corrected, then the substrate may be combined with other substrates, and additional printed circuit board processing steps, such as application of a solder mask, may be performed to produce a completed printed circuit board.

It will be appreciated by person skilled in the art that the present invention is not limited by what has been particularly shown and described herein above. Rather the scope of the present invention is defined only by the claims that follow:

What is claimed is:

1. A system comprising:
  a chassis, comprising:
    a first station comprising an automatic optical inspection (AOI) device which performs AOI of an electrical circuit to identify candidate defects on the electrical circuit, and
    a second station comprising a verification device which performs verification of candidate defects identified by the AOI device;
  a first transportable support table which supports and transports a first electrical circuit between the first station and the second station;
  a second transportable table which supports and transports a second electrical circuit between the first station and the second station; and
  a controller which controls the first transportable table and the second transportable table;
  wherein AOI is performed on the first and second electrical circuits and verification is performed on the first and second electrical circuits without changing a relative height of the AOI device with respect to the chassis and without changing a relative height of the verification device with respect to the chassis.

2. The system of claim 1, wherein the AOI device of the first station and the verification device of the second station are operable to respectively perform AOI and verification simultaneously.

3. The system of claim 1, wherein the AOI device comprises an image acquisition device comprising a charge coupled device (CCD) array.

4. The system of claim 3, further comprising a computer image processor, in operational communication with the AOI device, which outputs a report indicating suspected defects in an electrical circuit inspected by the AOI device.

5. The system of claim 1, wherein the verification device comprises an image acquisition device which acquires an image of a candidate defect in an electrical circuit and an image display device which displays the acquired image to an operator.

6. The system of claim 1, wherein the verification device comprises an automatic verification device which automatically verifies, without input from an operator, whether a candidate defect identified by the AOI means is a correctable real defect, a non-correctable real defect, or a false defect.

7. The system of claim 6, wherein the verification device is positioned a sufficient distance from an electronic circuit being verified that the operator may manually correct a defect on the electronic circuit.

8. The system of claim 1, wherein the chassis further comprises:
a third station comprising a correction device which corrects defects on the electrical circuits.

9. The system of claim 1, wherein each of the first transportable support table and the second transportable support table move in a first plane when moving towards the second station and move in a second plane, different form the first plane, when moving away from the second station.

10. The system of claim 9, wherein each of the first transportable support table and the second transportable support table moves from the second plane to the first plane upon reaching the first station.

11. A system comprising:
a chassis, comprising;
an automatic optical inspection (AOI) means for performing AOI of an electrical circuit to identify candidate defects on the electrical circuit, and
a verification means for performing verification of the candidate defects identified by the AOI means;
a first transport means for supporting and transporting an electrical circuit between the AOI means and the verification means;
a second transport means for supporting and transporting an electrical circuit between the AOI means and the verification means; and
a controller means for controlling the first transport means and the second transport means;
wherein the AOI means comprises means for performing AOI without changing a relative height of the AOI means with respect to the chassis; and
wherein the verification means comprises means for performing verification without changing a relative height of the verification means with respect to the chassis.

12. The system of claim 11, further comprising output means, in operational communication with the AOI means, for outputting a report indicating a suspected defect in an electrical circuit inspected by the AOI means.

13. The system of claim 11, wherein the verification means comprises:
image acquisition means for acquiring an image of a candidate defect in an electrical circuit; and
display means for displaying the image to an operator.

14. The system of claim 11, wherein the verification means comprises automatic verification means for automatically verifying, without input from an operator, whether a candidate defect identified by the AOI means is a correctable real defect, a non-correctable real defect, or a false defect.

15. The system of claim 14, wherein the verification means further comprises:
means for correcting correctable real defects; and
means for discarding an electrical circuit including a non-correctable real defect.

16. The system of claim 11, wherein each of the first transport means and the second transport means is operable to move in a first plane when moving towards the verification means and are operable to move in a second plane, different form the first plane, when moving away from the verification means.

17. The system of claim 16, wherein each of the first transport means and the second transport means are operable to move from the second plane to the first plane upon reaching the first AOI means.

* * * * *